United States Patent [19]

Becker et al.

[11] Patent Number: 5,399,562
[45] Date of Patent: Mar. 21, 1995

[54] INDOLONES USEFUL AS SEROTONERGIC AGENTS

[75] Inventors: Daniel P. Becker, Glenview; Daniel L. Flynn, Mundelein; Clara I. Villamil, Glenview, all of Ill.

[73] Assignee: G. D. Searle & Co., Chicago, Ill.

[21] Appl. No.: 191,840

[22] Filed: Feb. 4, 1994

[51] Int. Cl.$^6$ .................. A61K 31/44; C07D 471/18; C07D 451/04; C07D 453/00
[52] U.S. Cl. .................. 514/278; 514/214; 514/294; 514/304; 514/305; 514/409; 514/413; 540/543; 540/581; 546/15; 546/79; 546/97; 546/101; 546/126; 546/133; 546/137; 548/411; 548/455; 548/460
[58] Field of Search .............. 540/543, 581; 546/15, 546/79, 97, 101, 126, 133, 137; 548/411, 455, 460; 514/214, 278, 294, 304, 305, 409, 413

[56] References Cited

U.S. PATENT DOCUMENTS

| | | | |
|---|---|---|---|
| 5,063,231 | 11/1991 | Sanger et al. | 514/214 |
| 5,137,893 | 8/1992 | Becker et al. | 514/293 |
| 5,196,547 | 3/1993 | Becker et al. | 548/453 |
| 5,200,413 | 4/1993 | King et al. | 514/299 |
| 5,219,850 | 6/1993 | Becker et al. | 514/214 |
| 5,227,377 | 7/1993 | Flynn et al. | 514/214 |
| 5,260,303 | 11/1993 | Becker et al. | 514/300 |
| 5,280,028 | 1/1994 | Flynn et al. | 514/294 |
| 5,280,029 | 1/1994 | Becker et al. | 514/300 |

FOREIGN PATENT DOCUMENTS

| | | |
|---|---|---|
| 8767121 | 7/1987 | Australia . |
| 189002 | 7/1986 | European Pat. Off. . |
| 247266 | 12/1987 | European Pat. Off. . |
| 287196 | 10/1988 | European Pat. Off. . |
| 403882 | 12/1990 | European Pat. Off. . |
| 2152049 | 7/1985 | United Kingdom . |
| 2193633 | 2/1988 | United Kingdom . |
| 2231265 | 11/1990 | United Kingdom ........ A61K 31/55 |
| WO92/06689 | 4/1992 | WIPO . |
| WO92/14733 | 9/1992 | WIPO . |
| WO93/07147 | 4/1993 | WIPO . |

OTHER PUBLICATIONS

Bick et al. "Aristofruticosine . . . ," Tetrahed. Lett., vol. 29, No. 27, pp. 3355–3356 (1988).
Bok et al. "3-Azanoradamantanes," Heterocycles, vol. 12, No. 3, pp. 343–347 (1979).
Beerli et al. "Synthesis of Aristotelia . . . ," Helv. Chim. Acta, vol. 74, pp. 110–116 (1991).

*Primary Examiner*—Bernard Dentz
*Attorney, Agent, or Firm*—Cynthia S. Kovacevic; Roger A. Williams

[57] ABSTRACT

This invention relates to compounds of the formula:

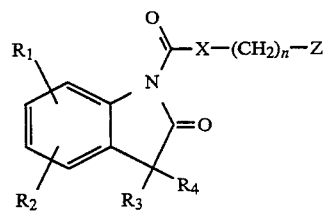

which are useful as 5-HT$_4$ agonists or antagonists and 5-HT$_3$ antagonists.

21 Claims, No Drawings

INDOLONES USEFUL AS SEROTONERGIC AGENTS

BACKGROUND OF THE INVENTION

The present invention relates to pharmaceutical agents (compounds) which act as 5-HT$_4$ agonists or antagonists and/or 5-HT$_3$ antagonists in mammals. As serotonin 5-HT$_4$ agonists, these compounds are gastrointestinal prokinetic agents useful for the treatment of human gastrointestinal (GI) hypomotility disorders such as reflux esophagitis, gastroparesis, nonulcer dyspepsia, ileus, constipation and irritable bowel syndrome (constipation predominant). As serotonin 5-HT$_4$ antagonists these compounds are useful in the treatment of motility disorders of the GI tract such as diarrhea and irritable bowel syndrome (diarrhea predominant). As serotonin 5-HT$_3$ antagonists these compounds are useful in slowing colonic transport and therefore are useful in the treatment of diarrhea predominant irritable bowel syndrome. The serotonin 5-HT$_4$ agonists or antagonists and/or serotonin 5-HT$_3$ antagonists are also useful in the treatment of emesis, anxiety, visceral pain, substance abuse (either cravings or withdrawal syndrome), cognitive disorders and other CNS disorders wherein treatment with a serotonin 5-HT$_4$ agonist or antagonist and/or serotonin 5-HT$_3$ antagonist would be indicated.

Serotonin (5-hydroxytryptamine; 5-HT) functions as a neurotransmitter in the mammalian central nervous system (CNS) and in the periphery. Serotonin is unsurpassed among monoamine neurotransmitters in the number of receptor subtypes identified. To date, the number of subtypes is into the teens, including the major subtypes 5-HT1A, 1B, 1C, 1D, 1E, 2A, 2B, 3 (perhaps subtypes), 1P, serotonin transporter, and recently 5-HT$_4$ (vida infra). Because of the multiplicity of serotonin receptor subtypes, the identification of which serotonin receptor subtype is correlated to various physiological/pharmacological actions is complicated.

Serotonin has been known for some years to promote peristalsis in the GI tract in various animal models. During the mid 1980s, several specific antagonists to the 5-HT$_3$ receptor subtype were identified from independent laboratories. These 5-HT$_3$ antagonists were shown to be prokinetic in various rodent models. Hence, many publications and patents have issued wherein 5-HT$_3$ antagonists are claimed to be useful as GI prokinetic agents to treat various human hypomotility states: reflux esophagitis, nonulcer dyspepsia, gastroparesis, ileus, irritable bowel syndrome.

Gunning and Naylor (J. Pharm. Pharmacol. 1985, 37, 78) reported that metoclopramide (a 5-HT$_3$ antagonist which blocks the 5-HT$_3$-mediated Bezold Jarisch reflex) enhanced electrical-field stimulated contractions in guinea pig stomach strips. Simultaneously, Buchheit et al. (J. Pharm. Pharmacol. 1985, 37, 664) reported that three 5-HT$_3$ antagonists [metoclopramide, ICS-205930, and MDL 72222] both enhanced guinea pig stomach muscle strip contraction in vitro and led to increases in gastric emptying rates in vivo. H. Kimura et al. (*Jpn. J. Pharmacol.*, 49 (suppl.) Mar. 25-28, 1989, 196pp) independently reported that SN-307, a selective 5-HT$_3$ antagonist, enhanced transit of a charcoal meal in mice. J. S. Gidda et al. (Gastroenterology 1988, 95, A867) reported that several 5-HT$_3$ antagonists [ICS-205930, GR38032, and zacopride] enhanced gastric emptying. From these reports it was concluded that serotonin 5-HT$_3$ antagonists would be useful agents for the therapeutic treatment of human GI dysmotilities where restoration of peristalsis and enhancement of transit is indicated.

More recently several clinical reports indicate that 5-HT$_3$ antagonists do not accelerate GI transit in man. Talley et al. (Digestive Diseases and Sciences 1989, 34, 1511) has reported that GR38032, a selective 5-HT$_3$ antagonist, did not alter small intestinal transit times or mouth-to-cecum transit times. The conclusion was that GR38032 does not have a major effect on GI transit in man. Another clinical report by S. Gore et al. (Aliment. Pharmacol. Therap. 1990, 4, 139) has demonstrated that GR38032 not only failed to accelerate GI transit, but in fact slowed colonic transit in man. Thus while 5-HT$_3$ antagonists do accelerate GI transit in rodent species (guinea pig, mouse, rat), they do not affect small bowel transit in man, and decrease, rather than increase, colonic transit.

Canine models of GI transit may more accurately reflect human results. J. M. Van Nueten et al. (British J. Pharmacology, 1989, 96, 331P) reported recently that cisapride (a reported 5-HT$_3$ antagonist) enhanced antroduodenal motility in dogs, whereas ICS-205930, another potent 5-HT$_3$ antagonist did not. Moreover, ICS-205930 did not affect the responses to cisapride when the agents were coadministered. Nemeth and Gullikson (European J. Pharmacology, 1989, 166, 387) reported that the ability of BRL-24924 and cisapride to depolarize myenteric neurons was unrelated to their properties of 5-HT$_3$ antagonism.

The receptor mechanism by which cisapride, BRL-24924, metoclopramide, and other serotonergic agents are prokinetic is not related to their 5-HT$_3$ antagonist properties. The receptor mechanism responsible for their prokinetic activities is serotonergic, but at a serotonin receptor subtype, presently referred to as 5-HT$_4$. (M. Tonini et al. Pharmacological Research, 1991, 24, 5).

Initially this clarification came from the laboratory of A. Dumuis, M. Sebben and J. Bockaert (Naunyn-Schmiedeberg's Arch. Pharmacol., 1989, 340, 403). The prokinetic activity of a variety of benzamides, including cisapride and BRL-24924, were found to correlate with agonist activity at a novel 5-HT$_4$ receptor subtype identified in mouse embryonic colliculi neurons. Shortly thereafter, D. Craig and D. Clarke identified the 5-HT$_4$ receptor in the myenteric plexus of the guinea pig ileum (J. Pharmacol. Exp. Ther., 1990, 252, 1378). Quite recently Craig and Clarke also demonstrated that the peristaltic reflex evoked by serotonin and the benzamide BRL-24924 (renzapride) was mediated through agonism at 5-HT$_4$ receptors.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, *Clinical Neuropharmacology*, Vol. 14, No. 1, pp. 1-16 (1991).

European Patent application 309,423 discloses azabicyclo substituted benzimidazoline-2-oxo-1-carboxylic acid derivatives which are useful as 5-HT receptor antagonists. Dumuis et al., Nauyn-Schmiedeberg's Arch. Pharmacol., (1991) 343:245-251 disclose azabicycloalkyl benzimidazolone derivatives as potent agonists at the 5-HT$_4$ receptor. In Pharmacological Research., Vol. 22, Supplement 2, (1990) Schiantarelli et al. disclose two benzimidazolone compounds useful as 5-HT₃ antagonists and 5-HT₃ agonists. U.S. Ser. No. 07/903,833 and U.S. Pat. No. 5,280,028 describe benzimidazole compounds which are useful as 5-HT₄ agonists or antagonists and/or 5-HT₃ antagonists.

WO 9214733, WO 9206689, EP 403,882, EP 247,266, EP 287,196, U.S. Pat. No. 5,200,413, U.S. Pat. No. 5,063,231, and AU 8,767,121 disclose N-azabicyclic substituted indole-1-carboxamides useful as 5-HT antagonists.

U.S. Pat. No. 5,260,303, WO 92/15593 and U.S. Ser. No. 07/973,126 disclose azacyclic substituted imidazopyridines useful as 5-HT₃ antagonists. U.S. Ser. No. 07/973,090 describes meso-azacyclic aromatic acid amides and U.S. Pat. No. 5,140,023 and U.S. Pat. No. 5,223,613 disclose azatetracyclic compounds.

Accordingly, it is the object of this invention to produce compounds for use as pharmaceutical agents which will exhibit 5-HT₄ serotonin agonist or antagonist activity and/or 5-HT₃ serotonin antagonist activity in mammals. The compounds of the present invention meet the need for an agent which has broad clinical usefulness for treating conditions affected by 5-HT₄ agonists or antagonists and/or 5-HT₃ antagonists in mammals.

SUMMARY OF THE INVENTION

This invention relates to compounds of the formula I

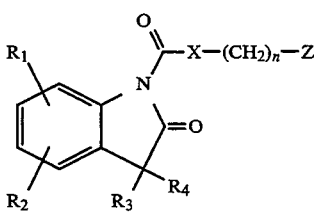

or a pharmaceutically acceptable salt thereof wherein Z is selected from the group consisting of Z-1

Z-2

Z-3
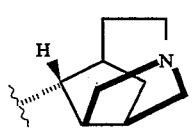

Z-4

Z-6
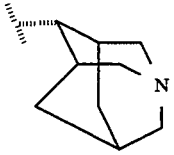

Z-7
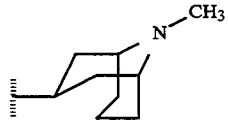

Z-8

Z-9
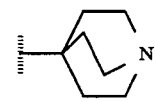

Z-10
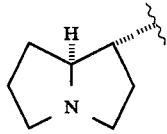

Z-11
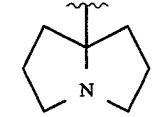

$R_1$ and $R_2$ are independently H, halogen, alkyl, aralkyl, amino, alkoxy, alkylthio, acylamino, hydroxy, nitro, aminocarbonyl, or aminosulfonyl;

$R_3$ and $R_4$ are independently H, $C_{1-6}$ alkyl, or together comprise $C_{2-5}$ cycloalkyl, optionally substituted by $C_{1-6}$ alkyl;

$X = NR_5$ or $O$;

n is 0, 1 or 2; and $R_5$ is hydrogen or alkyl of one to six carbon atoms.

The present invention also provides pharmaceutical compositions comprised of a therapeutically effective amount of the compounds of Formula I in combination with a pharmaceutically acceptable carrier and a method for treating conditions responsive to a 5-HT₄ serotonin agonist or antagonist and/or a 5-HT₃ serotonin antagonist compositions.

DETAILED DESCRIPTION OF THE INVENTION

This invention encompasses compounds of the Formula I as previously described.

Within the class of compounds defined by Formula I, there is a sub-class of preferred compounds represented by Formula:

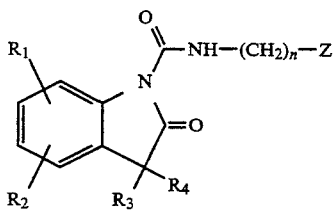

or a pharmaceutically acceptable salt thereof wherein

R₁ and R₂ are hydrogen;

R₃ and R₄ are both methyl or together form a cyclopropyl;

n is 0, 1 or 2; and

Z is selected from the group consisting of Z-1, Z-2, Z-6, Z-8, Z-9, Z-10 and Z-11.

Included within the preferred subclass of compounds of the Formula II are:

endo-2,3-dihydro-3,3-dimethyl-N-(8-methyl-8-azabicyclo[3.2.1]octan-3-yl)-2-oxo-1H-indole-1-carboxamide, hydrochloride hydrate;

endo-1',2'-dihydro-N-(8-methyl-8-azabicyclo[3.2.1]octan-3-yl)-2'-oxo-spiro[cyclopropane-1,3'-(3'H)-indole]-1'-carboxamide, hydrate hydrochloride;

anti-N-(1-azatricyclo[3.3.1.1³,⁷]decan-4-yl)-2'-oxospiro[cyclopropane-1,3'-[3'H]indole]-1'(2'H)-carboxamide, monohydrochloride;

syn-N-(1-azatricyclo[3.3.1.1³,⁷]decan-4-yl)-2'-oxospiro[cyclopropane-1,3'-[3'H]indole]-1'(2'H)-carboxamide, monohydrochloride;

N-(1-azabicyclo[2.2.2]octan-4-yl methyl)-2'-oxospiro[cyclopropane-1,3'-(3'H]indole]-1'(2'H)-carboxamide, monohydrochloride;

2'-oxo-N-[(hexahydro-1H-pyrrolizin-7a(5H)-yl)methyl]spiro[cyclopropane-1,3'-[3'H]indole]-1'(2'H)-carboxamide, monohydrochloride;

2'-oxo-N-[2-(hexahydro-1H-pyrrolizin-7a(5H)-yl)ethyl]spiro[cyclopropane-1,3'-[3H]indole]-1'(2'H)-carboxamide, monohydrochloride;

exo-2,3-dihydro-3,3-dimethyl-N-[(tetrahydro-1H-pyrrolizin-1S-yl)methyl]-2-oxo-1H-indole-1-carboxamide, hydrate hydrochloride; and 2,3-dihydro-3,3-dimethyl-N-(hexahydro-1H-2,5-methanocyclopenta[c]pyrrol-4R-yl)-2-oxo-1H-indole-1-carbooxamide, hydrate hydrochloride.

Included within the classes and subclasses of compounds embraced by Formulas I-II are pharmaceutically acceptable salts of such compounds.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al , "Pharmaceutical Salts," *J. Pharm. Sci.*, 66:1-19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying, formulating, or transporting a chemical agent.

The term "therapeutically effective amount" shall mean that amount of drug or pharmaceutical agent that will elicit the biological or medical response of a tissue, system or animal (mammal) that is being sought by a researcher or clinician.

The term "alkyl" as used herein means a univalent hydrocarbon radical having from one to six carbon atoms, derived by the removal of a single hydrogen atom from a straight or branched chain saturated hydrocarbon. Representative of such radicals are methyl, ethyl, n-propyl, isopropyl, n-butyl, sec-butyl, isobutyl, tert-butyl, 2-methylpentyl and the like.

The term "alkoxy" as used herein means an alkyl radical, as defined above having one or more oxygen atoms attached thereto. Representative alkoxy groups include methoxy, ethoxy, propoxy, tert-butoxy and the like.

The term "halogen" or "halo" as used herein means a fluoro, chloro, bromo or iodo radical.

The term "amino" as used herein is represented by the radical —NR₈R₉ wherein R₈ and R₉ are independently hydrogen or an alkyl group as previously described.

The term "acylamino" as used herein is represented by the radical

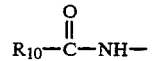

wherein R₁₀ is an alkyl group as described above.

The term "aminosulfonyl" as used herein is represented by the radical R₈R₉N—SO₂— wherein —NR₈R₉ is an amino group as defined above.

The term "aminocarbonyl" as used herein is represented by the radical

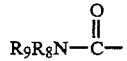

wherein —NR₈R₉ is an amino group as defined above.

The term "alkylthio" as used herein is represented by a radical of the formula R₁₁—S—, wherein R₁₁ is an alkyl group as defined above.

The term "aralkyl" as used herein is represented by an aryl group, such as phenyl or pyridyl, attached to the compound via an alkylene moiety.

The term "C₂₋₅ cycloalkyl" as used herein means an alicyclic unsaturated 2 to 5 membered carbon radical represented by groups such as cyclopropyl, cyclobutyl and cyclopentyl.

The compounds herein exhibit 5-HT₄ agonism or antagonism and/or 5-HT₃ antagonism. The 5-HT₃ activity possessed by the compounds of this invention was determined by the radioligand receptor binding assay as described herein. The 5-HT₄ agonist activity was determined in the in vitro rat tunica muscularis mucosae (TMM) assay described herein. (Baxter et al., Naunyn Schmied Arch. Pharmacol, 1991, 343, 439). Similarly, use of the rat TMM assay may be employed to identify 5-HT₄ antagonists which block the action of serotonin. One with skill in the art could determine the activity of the compounds of the present invention using the methodology of these assays, described herein, without undue experimentation.

By virtue of their activity as 5-HT₄ agonists or antagonists and/or 5-HT₃ antagonists the compounds of Formula I and II are useful in treating conditions such as gastrointestinal motility disorders, emesis, anxiety, cognitive disorders and other CNS disorders. As used herein gastrointestinal motility disorders responsive to treatment with 5-HT$_4$ agonists include reflux esophagitis, non-ulcer dyspepsia, gastroparesis, ileus, irritable bowel syndrome (constipation predominant), constipation, and the like. As used herein gastrointestinal motility disorders responsive to treatment with 5-HT$_4$ antagonists include diarrhea, irritable bowel syndrome (diarrhea predominant) and the like. As used herein disorders responsive to 5-HT$_3$ antagonists include emesis due to either cancer chemotherapy or operative procedures, anxiety, cognitive disorders, drug abuse (either cravings or withdrawal syndrome), irritable bowel syndrome (diarrhea predominant) and the like. A physician or veterinarian of ordinary skill can readily determine whether a subject exhibits such a condition treatable with a 5-HT$_4$ agonist or antagonist or a 5-HT$_3$ antagonist. The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known in the pharmaceutical art. In general, the preferred form of administration is oral.

For the orally administered pharmaceutical compositions and methods of the present invention, the foregoing active ingredients will typically be administered in admixture with suitable pharmaceutical diluents, excipients or carriers (collectively referred to herein as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosages for preventing or treating conditions mediated by 5-HT$_4$ agonists or antagonists and/or 5-HT$_3$ antagonists with the compounds of the present invention are determined in accordance with a variety of factors, including the type, age, weight, sex and medical condition of patient, the severity of the condition, the route of administration and the particular compound employed in the treatment. A physician or veterinarian of ordinary skill can readily determine and prescribe the effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, and more preferably in the range of about 10 to 500 mg.

The compounds of the present invention are prepared according to the following reaction schemes I–II. According to Scheme I, a solution of the appropriate amine Z-(CH$_2$)$_n$-NH$_2$ and triethylamine in toluene is treated sequentially with triphosgene and indolone A to yield the desired urea II. Alternatively, a solution of indolone A and triethylamine in toluene is treated sequentially with triphosgene and the appropriate amine Z-(CH$_2$)$_n$-NH$_2$ to yield the desired urea II. Also effective for the preparation of II is deprotonation of indolone A with sodium hydride in THF followed by sequential treatment of the salt with phosgene in toluene and the appropriate amine Z-(CH$_2$)$_n$-NH$_2$. Scheme II describes the preparation of indolones of the formula III. Accordingly, indolone A is treated with phosgene or a phosgene equivalent, such as triphosgene, in the presence of triethylamine in an inert solvent such as toluene or THF followed by treatment with a metal salt (M=Na, K, or Cs) of the appropriate alcohol Z-(CH$_2$)$_n$-OM.

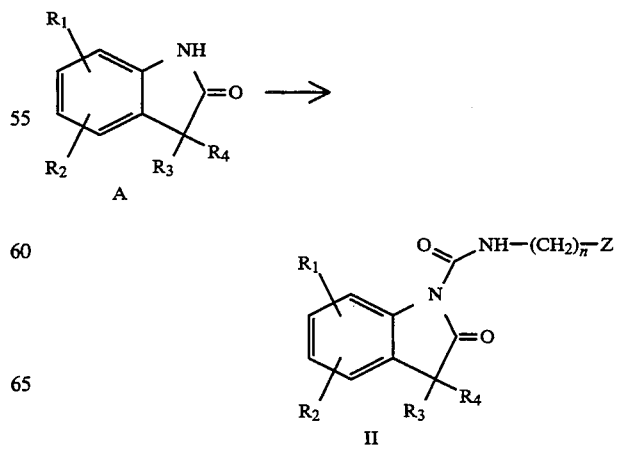

SCHEME I

SCHEME II

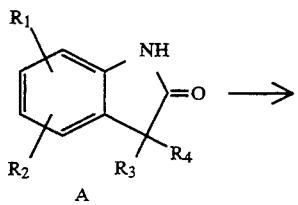

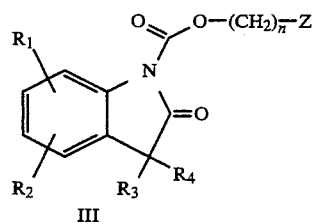

EXAMPLE A

4-Aminomethylquinuclidine

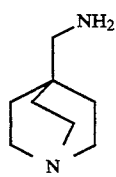

To a solution of 4-cyanoquinuclidine (500 mg, 3.64 mmol, prepared by the method described in EP-269,991-A) in dry THF (5 mL) was added a 1M solution of lithium aluminum hydride (8 mL, 8.0 mmol). The reaction was heated under reflux for 2.5 hours, then subjected to a Fieser workup to yield 4-aminomethylquinuclidine (460 mg, 91%).

| Analysis calculated for $C_8H_{16}N_2*1.9HCl*0.25H_2O$: | | |
|---|---|---|
| | Calc | Found |
| C | 44.90 | 44.52 |
| H | 8.67 | 8.53 |
| N | 13.09 | 12.90 |
| Cl | 31.33 | 31.48 |

EXAMPLE 1

Endo-2,3-dihydro-3,3-dimethyl-N-(8-methyl-8-azabicyclo[3.2.1]octan-3-yl)-2-oxo-1H-indole-1-carboxamide, hydrochloride hydrate

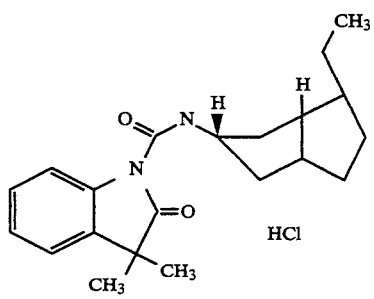

To a solution of endo-3-aminotropane (69 mg, 0.489 mmol; prepared in accordance with the procedure in *J. Am. Chem. Soc.* 1957, 79, 4194) and triethylamine (99 mg, 0 978 mmol) in toluene (2 mL) at 0° C., was added a solution of triphosgene (48 mg, 0.16 mmol) in toluene (1 ml) and the solution was warmed to room temperature over 0.5 hour. A suspension of 1,3-dihydro-3,3-dimethyl-2H-indol-2-one (79 mg, 0.49 mmol) prepared by the method of Robertson (*J. Med. Chem.* 1986, 29, 1832) in toluene (1 ml) was then added and the reaction was stirred for 3 hours at room temperature and then heated under reflux for 3 hours. Water was added and the organic layer was separated. The aqueous layer was then extracted with CHCl₃ (3X). After basification with 2N KOH (1.5 ml) the aqueous layer was again extracted with CHCl₃(2X). The combined organic layers were washed with H₂O and brine and dried (Na₂SO₄) and concentrated to give a residue (130 mg) which was chromatographed on silica gel eluting with 2/98 MeOH(NH₃)/CHCl₃ to given the desired compound (61 mg, 38%) as the free base. A solution of the free base (129 mg, 0.39 mmol) in MeOH (2 ml) from two separate runs was treated with methanolic HCl [prepared by the addition of acetyl chloride (36 mg, 0.51 mmol) to MeOH (2 ml)]. Concentration gave a residue which was crystallized from MeOH/Et₂O to give the title compound (125 mg, 86%) as a colorless powder: mp 229°–230° C.

| Analysis calculated for $C_{19}H_{25}N_3O_2*HCl*0.2H_2O$: | | |
|---|---|---|
| | Calc | Found |
| C | 62.10 | 62.18 |
| H | 7.24 | 7.21 |
| N | 11.44 | 11.33 |
| Cl | 9.65 | 9.91 |

EXAMPLE 2

Endo-1',2'-dihydro-N-(8-methyl-8-azabicyclo[3.2.1 octan-3-yl)-2'-oxo-spiro[cyclopropane-1,3'-(3'H)-indole]-1'-carboxamide, hydrate hydrochloride

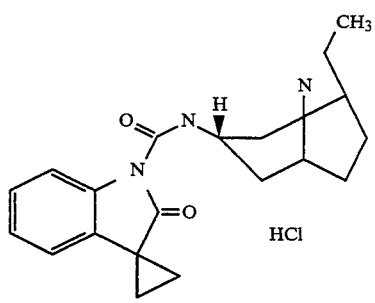

To a solution of spiro[cyclopropane-1,3'-[3'H]indole]-2'(1'H)-one (130 mg, 0.806 mmol) prepared by the method of Robertson (*J. Med Chem.* 1987, 30, 824) and triethylamine (163 mg, 1.61 mmol) in toluene (1 ml) at 0° C. was added a solution of triphosgene (79 mg, 0.266 mmol) in toluene (1 ml) and the solution was allowed to warm to room temperature over 0.5 hour. A solution of endo-3-aminotropane (79 mg, 0.49 mmol) in toluene (1 ml) was then added and the reaction was stirred for 1 hour at room temperature and then heated under reflux for 5 hours. Water was added and the organic layer was separated. The aqueous layer was then basified with 2N KOH (1.5 ml) and extracted with CHCl₃ (3X). The combined organic layers were washed with H₂O and brine and dried (Na$_2$SO$_4$) and concentrated to give a residue (206 mg) which was chromatographed on silica gel eluting with 2/98 MeOH(NH$_3$)/CHCl$_3$ to give the desired compound (80 mg, 30%) as the free base: mp 160°–162° C. A solution of the free base (80 mg, 0.24 mmol) in MeOH (2 ml) was then treated with methanolic HCl [prepared by the addition of acetyl chloride (26 mg, 0.37 mmol) to MeOH (2 ml)]. Concentration gave a residue which was crystallized from MeOH/Et$_2$O to give the title compound (85 mg, 96%) as a colorless powder.

mp 239° C.

| Analysis calculated for C$_{19}$H$_{23}$N$_3$O$_2$*HCl*0.2H$_2$O: | | |
|---|---|---|
| | Calc | Found |
| C | 62.44 | 62.44 |
| H | 6.73 | 6.59 |
| N | 11.50 | 11.35 |
| Cl | 9.70 | 9.79 |

EXAMPLE 3

Anti-N-(1-azatricyclo[3.3.1.1$^{3,7}$]decan-4-yl)-2'-oxo-spiro[cyclopropane-1,3'-[3'H]indole]-1'(2'H)-carboxamide, monohydrochloride

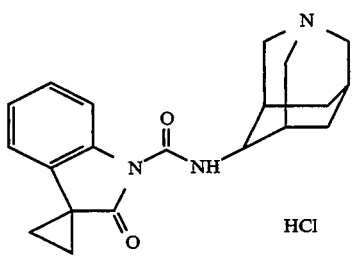

HCl

To sodium hydride (200 mg, 5.2 mmol, washed 2× with hexane) suspended in THF (4 ml) was added spiro[cyclopropane-1,3'-[3'H]indole]-2'(1H)-one (207 mg, 1.3 mmol) and the suspension was stirred for 15 minutes. To the resulting suspension was added a solution of 20% phosgene in toluene (5.14 ml, 10.4 mmol) in THF (0.5 ml) and the reaction was then stirred for 2 hours. Filtration through celite and concentration in vacuo gave a beige solid which was dissolved in THF (5 ml) and treated with a suspension of anti-N-(1-azatricyclo[3.3.1.1.$^{3,7}$]decane-4-amine (200 mg, 1.3 mmole) prepared by the method of Becker and Flynn [*Synthesis* 1992, 1080] and triethylamine (194 μl, 1.4 mmole) in THF (2 ml). The reaction was stirred for 18 hours and the suspension heated to 60° C. for 1 hour. Removal of the solvent gave a solid which was dissolved in chloroform, washed with saturated K$_2$CO$_3$, filtered and concentrated in vacuo to give the crude desired compound as a solid. Purification on silica gel eluting with 5% CH$_3$OH(NH$_3$)/CHCl$_3$ gave the desired compound (98 mg, 22%).

| Analysis calculated for C$_{20}$H$_{23}$N$_3$O$_2$*0.33H$_2$O, MW 343.42: | | |
|---|---|---|
| | Calc | Found |
| C | 69.95 | 69.98 |
| H | 6.94 | 6.89 |
| N | 12.23 | 11.93 |
| MS calculated for C$_{20}$H$_{23}$N$_3$O$_2$: | | 337.1790 |
| Found: | | 337.1800 |

The free base (91 mg, 0.270 mmole) was converted to the hydrochloride salt by dissolving in HCl/CH$_3$OH [prepared by the addition of acetyl chloride (21 μl 0.296 mmol) to CH$_3$OH (0.5 ml)]. Concentration in vacuo gave the desired hydrochloride salt (95 mg) as a solid.

| Analysis calculated for C$_{20}$H$_{23}$N$_3$O$_2$*HCl*1.5H$_2$O, MW 400.87: | | |
|---|---|---|
| | Calc | Found |
| C | 59.92 | 59.63 |
| H | 6.79 | 6.47 |
| N | 10.48 | 10.37 |
| Cl | 8.84 | 8.94 |
| MS calculated for C$_{20}$H$_{24}$N$_3$O$_2$: | | 338.1868 |
| Found: | | 338.1838 |

EXAMPLE 4

Syn-N-(1-azatricyclo[3.3.1.1$^{3,7}$]decan-4-yl)-2'-oxo-spiro[cyclopropane-1,3'-[3'H]indole]-1'(2'H)-carboxamide, monohydrochloride

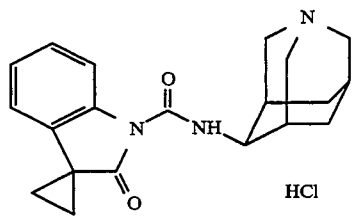

HCl

To a suspension of sodium hydride (200 mg, 5.2 mmol)(washed 2× with hexane) in THF (4 ml) was added spiro[cyclopropane-1,3'-[3'H]indole]-2'(1'H)-one (207 mg, 1.3 mmole) and stirred for 15 minutes. The resulting suspension was added to a solution of 20% phosgene in toluene (5.14 ml, 10.4 mmol) in THF (5 mL) and stirred for 2 hours. The reaction mixture was filtered through celite and concentrated in vacuo to give a beige solid which was dissolved in THF (5 ml) and treated with a suspension of syn-N-(1-azatricyclo[3.3.1.1.$^{3,7}$]decane-4 amine (235 mg, 1.3 mmol) prepared by the method of Becker and Flynn [*Synthesis* 1992, 1080] and triethylamine (194 μl, 1.4 mmol) in THF (2 ml) and stirred for 18 hours. The solvent was removed in vacuo to give a solid which was dissolved in chloroform, washed with saturated K$_2$CO$_3$ solution, dried over K$_2$CO$_3$, filtered and concentrated in vacuo to give the crude desired compound. Purification was performed on silica gel eluting with 5% CH$_3$OH(NH$_3$)/CHCl$_3$ to give the title compound (143 mg, 34%).

| Analysis calculated for C$_{20}$H$_{23}$N$_3$O$_2$, MW 337.40: | | |
|---|---|---|
| | Calc | Found |
| C | 71.19 | 70.84 |
| H | 6.87 | 7.01 |
| N | 12.45 | 12.21 |
| MS calculated for C$_{20}$H$_{23}$N$_3$O$_2$: | | 337.1790 |
| Found: | | 337.1786 |

The free base (160 mg, 0.477 mmole) was converted to the hydrochloride salt by treatment with methanolic HCl to give the monohydrochloride (171 mg, 96%) as a solid.

Analysis calculated for C$_{20}$H$_{23}$N$_3$O$_2$,*HCl*1.5H$_2$O, MW 400.87:

| | Calc | Found |
|---|---|---|
| C | 59.82 | 59.92 |
| H | 6.49 | 6.79 |
| N | 10.41 | 10.48 |
| Cl | 8.95 | 8.84 |
| MS calculated for C20H23N3O2: | | 337.1790 |
| Found: | | 337.1811 |

EXAMPLE 5

N-(1-azabicyclo[2.2.2]octan-4-ylmethyl)-2'-oxo-spiro[-cyclopropane-1,3'-[3'H]indole]-1'(2'H)-carboxamide, monohydrochloride

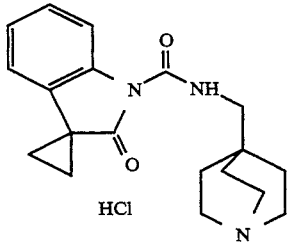

To sodium hydride (92 mg, 2.31 mmol) (washed 2× with hexane) suspended in THF (1 ml) was added spiro[cyclopropane-1,3'-[3'H]indol]-2'(1'H)-one (92 mg, 0.578 mmol) and the reaction was stirred for 5 minutes. The resulting suspension was added to a solution of 20% phosgene in toluene (2.29 ml, 4.62 mmol) in THF (2 mL) and stirred for 0.5 hour. The reaction mixture was then filtered through celite and concentrated in vacuo to give a beige solid which was dissolved in THF (5 ml) and treated with a solution of 4-aminomethyl quinuclidine (81 mg, 0.578 mmol) as prepared in Example A in THF (2 ml) and stirred for 18 hours. Concentration in vacuo gave a solid which was dissolved in chloroform, washed with 1N NaOH solution, dried over K2CO3, filtered and concentrated in vacuo to give the crude desired compound as a solid. Purification on silica gel eluting with 10% CH3OH(NH3)/CHCl3 gave the title compound (35 mg, 19%).

| MS calculated for C19H23N3O2: | 325.1790 |
|---|---|
| Found: | 325.1757 |

The free base (59 mg, 0.181 mmole) was converted to the hydrochloride salt by treatment with methanolic HCl to give the monohydrochloride (57 mg, 91%) as a solid.

| Analysis calculated for C19H23N3O2*HCl*.9H2O, MW 378.07: | | |
|---|---|---|
| | Calc | Found |
| C | 60.36 | 60.11 |
| H | 6.88 | 6.63 |
| N | 11.11 | 10.97 |
| Cl | 9.38 | 9.94 |
| MS calculated for C19H23N3O2: | | 325.1790 |
| Found: | | 325.1798 |

EXAMPLE 6

2'-oxo-N-[(hexahydro-1H-pyrrolizin-7a(5H)-yl)-methyl]spiro[cyclopropane-1,3'-[3'H]indole]1'(2'H)carboxamide, monohydrochloride

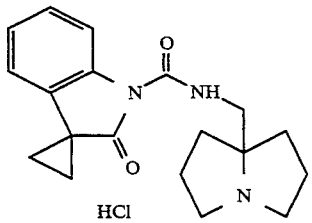

To sodium hydride (200 mg, 5.2 mmol, washed 2× with hexane) suspended in THF (5 ml) was added spiro[cyclopropane-1,3'-[3'H]indole]-2'(1'H)-one (207 mg, 1.3 mmol) and the reaction was stirred for 15 minutes. The resulting suspension was added to a solution of 20% phosgene in toluene (5.14 ml, 10.4 mmol) in THF (5 mL) and the reaction was then stirred for 2 hours. The reaction mixture was then filtered through celite and concentrated in vacuo to give a beige solid. To the solid dissolved in THF (5 ml) was added a suspension of 7a-aminomethyl-hexahydro-1H-pyrrolizine (200 mg, 1.4 mmol) [J. Het. Chem. 1987, Vol. 24, 47], triethylamine (197 μl, 1.3 mmol) in THF (2 ml) and stirred 18 hours. Concentration in vacuo gave a solid which was dissolved in chloroform, washed with saturated K2CO3 solution, dried over K2CO3, filtered and concentrated in vacuo to give the crude desired compound as a solid. Purification on silica gel eluting with 10% CH3OH(NH3)/CHCl3 gave the title compound (160 mg, 39%).

| Analysis calculated for C19H23N3O2*.1H2O, MW 327.20: | | |
|---|---|---|
| | Calc | Found |
| C | 69.74 | 69.61 |
| H | 7.15 | 7.29 |
| N | 12.84 | 12.79 |
| MS calculated for C19H24N3O2: | | 326.1868 |
| Found M + 1: | | 326.1883 |

The free base (147 mg, 0.450 mmol) was converted to the hydrochloride salt by treatment with methanolic HCl to give 149 mg (91%) as a solid.

| Analysis calculated for C19H23N3O2*HCl*.33H2O, MW 367.88: | | |
|---|---|---|
| | Calc | Found |
| C | 62.04 | 62.12 |
| H | 6.48 | 6.62 |
| N | 11.42 | 11.43 |
| Cl | 9.64 | 9.97 |
| MS calculated for C19H24N3O2: | | 326.1868 |
| Found M + 1: | | 326.1821 |

EXAMPLE 7

2'-oxo-N-[2-(hexahydro-1H-pyrrolizin-7a(5H)yl)ethyl]-spiro[cyclopropane-1,3'-[3'H]indole-1'(2'H)-carboxamide, monohydrochloride

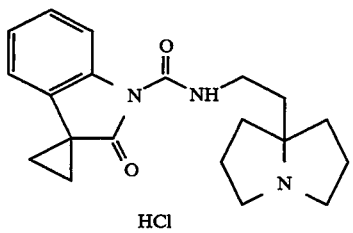

HCl

To sodium hydride (197 mg, 5.20 mmol, washed 2× with hexane) suspended in THF (5 ml) was added spiro[cyclopropane-1,3'-[3'H]indol]-2'(1'H)-one (205 mg, 1.29 mmol) and stirred for 10 minutes. The resulting suspension was then added to a solution of 20% phosgene in toluene (5.2 ml, 10.4 mmol) in THF (5.2 ml) and the reaction was stirred for 2 hours. The reaction mixture was then filtered through celite and concentrated in vacuo to give a beige solid. To a solution of the solid in THF (5 ml) was added a solution of 7a-aminoethyl-hexahydro-1H-pyrrolizine (200 mg, 1.4 mmol) [*J. Het. Chem.* 1987, Vol. 24, 271] and triethylamine (197 μl, 1.3 mmole) in THF (2 ml) and stirred for 18 hours. Concentration in vacuo gave a solid which was dissolved in chloroform, washed with saturated $K_2CO_3$ solution, dried over $K_2CO_3$, filtered and concentrated in vacuo to give the crude desired compound. Purification on silica gel eluting with 10% $CH_3OH(NH_3)/CHCl_3$ gave the title compound (192 mg, 44%).

| MS calculated for $C_{20}H_{25}N_3O_3$: | 339.1947 |
|---|---|
| Found: | 339.1958 |

The free base (179 mg, 0.526 mmol) was converted to the hydrochloride salt by treatment with methanolic HCl to give 160 mg (81%) as a solid.

| Analysis calculated for $C_{20}H_{24}H_3O_2*HCl*.8H_2O$, MW 390.21: | | |
|---|---|---|
| | Calc | Found |
| C | 61.55 | 61.11 |
| H | 7.13 | 6.89 |
| N | 10.77 | 10.60 |
| Cl | 9.08 | 9.68 |
| MS calculated for $C_{20}H_{25}N_3O_2$: | | 339.1947 |
| Found: | | 339.1963 |

EXAMPLE 8

Exo-2,3-dihydro-3,3-dimethyl-N-[(hexahydro-1H-pyrrolizin-1S-yl)methyl]-2-oxo-1H-indole-1carboxamide, hydrate hydrochloride

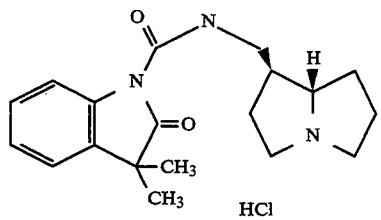

HCl

To sodium hydride (214 mg, 5.6 mmol, washed 2× with hexane) suspended in THF (1 ml) was added 1,3-dihydro-3,3-dimethyl-2H-indol-2-one (226 mg, 1.4 mmol) and the reaction was stirred for 10 minutes. The resulting suspension was added to a solution of 20% phosgene in toluene (5.50 ml, 11.2 mmol) in THF (5 mL) and stirred for 1 hour. The reaction mixture was filtered through celite and concentrated in vacuo to give an oil. To a solution of the oil in THF (5 ml) was added a solution of cis-3-amino-methyl-N-hexahydro-1H-pyrrolizine (200 mg, 1.4 mmol) prepared by the method of Flynn [*J. Med. Chem.* 1992, 35, 1486] and triethylamine (200 μl, 1.4 mmol) in THF (2 ml) and the reaction was stirred for 18 hours. The solution was then diluted with chloroform, washed with saturated $K_2CO_3$ solution, dried over $K_2CO_3$, filtered and concentrated in vacuo to give crude desired product as an oil. Purification on silica gel eluting with 10% $CH_3OH(NH_3)/CHCl_3$ gave the title compound (193 mg, 42%).

| Analysis calculated for $C_{19}H_{25}N_3O_2*.4H_2O$, MW 327.43: | | |
|---|---|---|
| | Calc | Found |
| C | 68.19 | 68.06 |
| H | 7.77 | 7.74 |
| N | 12.56 | 12.44 |
| MS calculated for $C_{19}H_{25}N_3O_2$: | | 327.1947 |
| Found: | | 327.1930 |

The free base (180 mg, 0.550 mmol) was converted to the hydrochloride salt by treatment with methanolic HCl to give 128 mg (64%) as a solid.

| Analysis calculated for $C_{19}H_{25}N_3O_2HCl*.25H_2O$, MW 368.37: | | |
|---|---|---|
| | Calc | Found |
| C | 61.95 | 61.54 |
| H | 6.98 | 6.92 |
| N | 11.41 | 11.36 |
| Cl | 9.62 | 9.90 |
| MS calculated for $C_{19}H_{25}N_3O_2$: | | 327.1947 |
| Found: | | 327.1939 |

EXAMPLE 9

2,3-dihydro-3,3-dimethyl-N-(hexahydro-1H-2,5-methanocyclopenta[c]pyrrol-4R-yl)-2-oxo-1H-indole-1-carboxamide, hydrate hydrochloride

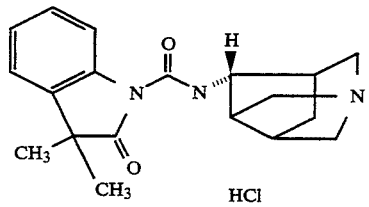

To sodium hydride (214 mg, 5.6 mmol, washed 2× with hexane) suspended in THF (5 ml) was added 1,3-dihydro-3,3-dimethyl-2H-indol-2-one (226 mg, 1.4 mmol) and the suspension stirred for 15 minutes. The resulting suspension was added to a solution of 20% phosgene in toluene (5.50 ml, 11.2 mmol) in THF (5 mL) and suspension stirred for 2 hours. The reaction mixture was filtered through celite and concentrated in vacuo to give an oil. To a solution of the oil dissolved in THF (5 ml) was added a solution of (+)-endo-N-hexahydro-1H-2,5β-methano-3aα,6aα-cyclopenta[c]pyrrol-4α-amine(193 mg, 1.4 mmol), prepared by the method described in U.S. Pat. No. 5,140,023, and triethylamine (200 μl, 1.4 mmol) in THF (2 ml) and the reaction was stirred for 18 hours. The reaction mixture was diluted with chloroform, washed with saturated $K_2CO_3$ solution, dried over $K_2CO_3$, filtered and concentrated in vacuo to give the crude desired compound as a solid. Purification on silica gel eluting with 10% $CH_3OH(NH_3)/CHCl_3$ gave the title compound (223 mg, 49%).

| Analysis calculated for $C_{19}H_{23}N_3O_2$*.$2H_2O$, MW 328.99: | | |
|---|---|---|
| | Calc | Found |
| C | 69.36 | 69.37 |
| H | 7.17 | 7.07 |
| N | 12.77 | 12.65 |
| MS calculated for $C_{19}H_{23}N_3O_2$: | | 325.1790 |
| Found: | | 325.1769 |

The free base (201 mg, 0.618 mmol) was converted to the hydrochloride salt by treatment with methanolic HCl to give 183 mg (82%) as a solid.

| Analysis calculated for $C_{19}H_{23}N_3O_2$*HCl*$1.4H_2O$, MW 387.08: | | |
|---|---|---|
| | Calc | Found |
| C | 58.95 | 58.62 |
| H | 6.98 | 6.69 |
| N | 10.86 | 10.67 |
| MS calculated for $C_{19}H_{23}N_3O_2$: | | 325.1790 |
| Found: | | 325.1779 |

EXAMPLE 10

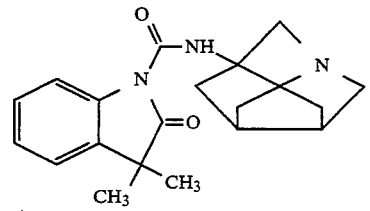

The title compound is prepared from 1,3-dihydro-3,3-dimethyl-2H-indol-2-one as described in Example 1 substituting the appropriate aminoazatricycle (prepared in accordance with the teaching of U.S. Pat. No. 5,137,893).

EXAMPLE 11

2,3-dihydro-3,3-dimethyl-N-(hexahydro-2,5-ethano-1H-3a,6a-cyclopenta[c]pyrrol-4R-yl)-2-oxo-1H-indole-1-carboxamide

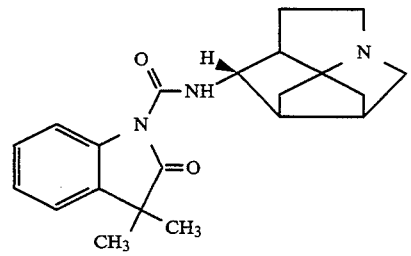

The title compound is prepared from 1,3-dihydro-3,3-dimethyl-2H-indol-2-one as described in Example 1 substituting the appropriate aminoazatricycle (prepared in accordance with the teaching of U.S. Pat. No. 5,233,613).

EXAMPLE 12

2,3-dihydro-3,3-dimethyl-N-(hexahydro-2,5-ethano-1H-3a,6a-cyclopenta[c]pyrrol-5-yl)-2-oxo-1H-indole-1-carboxamide

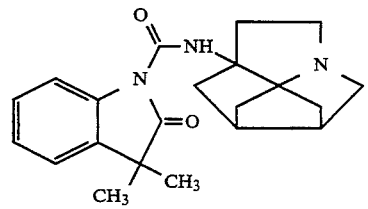

The title compound is prepared from 1,3-dihydro-3,3-dimethyl-2H-indole-2-one as described in Example 1 substituting the appropriate aminoazatricycle (prepared in accordance with the teaching of U.S. Pat. No. 5,137,893).

EXAMPLE 13

2,3-dihydro-3,3-dimethyl-N-(endo-9-methyl-9-azabicyclo [3.3.1]nonan-3-yl)-2-oxo-1H-indole-1-carboxamide

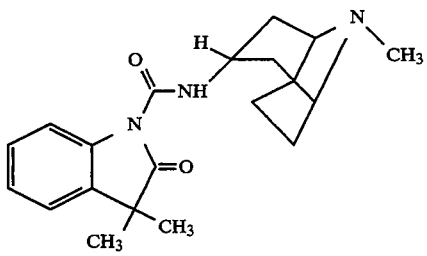

The title compound is prepared from 1,3-dihydro-3,3-dimethyl-2H-indol-2-one as described in Example 1 substituting endo-3-aminogranatane.

EXAMPLE 14

2,3-dihydro-3,3-dimethyl-O-(endo-8-methyl-8-azabicyclo[3.2.1]octan-3-yl)-2-oxo-1H-indole-1-carboxylate

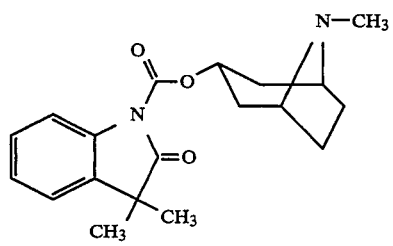

To a suspension of sodium hydride in THF is added 1,3-dihydro-3,3-dimethyl-2H-indol-2-one and the suspension is stirred for 15 minutes. To the resulting suspension is added a solution of 20% phosgene in toluene and the reaction is stirred for 2 hours. Filtration through celite and concentration in vacuo gives a residue which is dissolved in THF, cooled to −20° C., and treated with a THF solution of the lithium alkoxide of tropine (prepared by the treatment of a solution of tropine in THF with one equivalent of n-butyl lithium). The reaction is then stirred for 3 hours at room temperature. Removal of the solvent gives a residue which is dissolved in chloroform, washed with saturated $K_2CO_3$, filtered and concentrated in vacuo. Purification on silica gel eluting with 5% $CH_3OH(NH_3)/CHCl_3$ gives the title compound.

A. In Vitro Functional Assay for Serotonin 5-HT$_4$ agonism: RAT TMM

Serotonin 5-HT$_4$ agonism was measured in the rat esophagus in vitro preparation as reported by Baxter et al. (Naunyn. Schmied. Arch. Pharmacol. 1991, 343, 439). Agonist activity was determined utilizing relaxation of carbachol-contracted rat tunica muscularis mucosae (TMM). One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 μM) and fluoxetine (1 μM) were included in the buffer to prevent uptake of serotonin, as well as pargyline (10 μM) to inhibit monoamine oxidase. Following a 30 min equilibrium period, tissues were isometrically contracted with carbachol (3 μM) to obtain a tonic contraction. A stable plateau was obtained within 20 min when test compound was added cumulatively to relax the muscle strip. EC$_{50}$ values were obtained for each compound in tissues from 5 rats. EC$_{50}$ values for agonists at this 5-HT$_4$ receptor are indicated in Table I.

TABLE I

| Compound | 5-HT$_4$ Agonism (Rat TMM) In Vitro Assay: EC50 values |
|---|---|
| Serotonin | 9 nM |
| Example 1 | 1214 nM |
| Example 2 | 790 nM |
| Example 3 | 2216 nM |
| Example 4 | 2526 nM |
| Example 5 | >10,000 nM |
| Example 6 | >10,000 nM |
| Example 7 | 7915 nM |
| Example 8 | >10,000 nM |
| Cisapride | 55 nM | b. Serotonin (5-HT$_3$)

Procedure: GR65630 binds to the 5-HT$_3$ receptor. Brain cortices were obtained from male rats and a membrane fraction prepared by standard techniques. 0.04 mg of membrane prep was incubated with 0.2 nM [$^3$H]-GR65630 for 66 minutes at 22° C. Non-specific binding was estimated in the presence of 1 uM ICS 205-930. Membranes were filtered and washed 3 times and the filters were counted to determine [$^3$H]-GR65630 specifically bound. [Kilpatrick GJ, Jones BJ and Tyers MB, Identification and Distribution of 5-HT$_3$ Receptors in Rat Brain Using Radioligand Binding Assay, Nature, 330, 746–748 (1987)].

Results: $K_d$=2.46 $B_{max}$=154 fmol/mg protein
% Specific Binding: 70

TABLE II

| Effect of Compounds on [H]-GR65630 Bound (0.2 nM) | |
|---|---|
| Compound | Ki |
| Cisapride | 1500 nM |
| Example 1 | 4.0 nM |
| Example 2 | 4.1 nM |
| Quipazine | 0.18 nM |
| ICS 205-930 | 0.51 nM |
| 5-HT | 0.39 uM |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

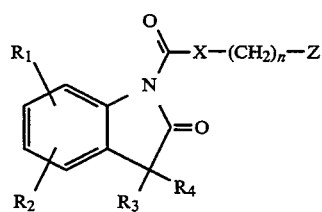

or a pharmaceutically acceptable salt thereof wherein Z is selected from the group consisting of

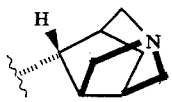
Z-1

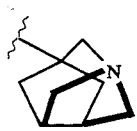
Z-2

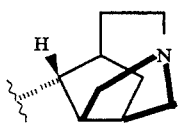
Z-3

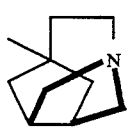
Z-4

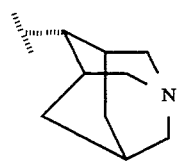
Z-6

Z-7

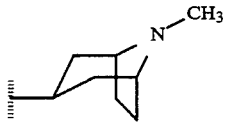
Z-8

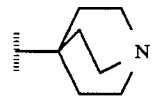
Z-9

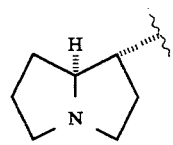
Z-10

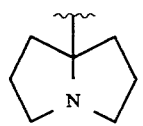
Z-11

$R_1$ and $R_2$ are independently H, halogen, alkyl, aralkyl, amino, alkoxy, alkylthio, acylamino, hydroxy, nitro, aminocarbonyl, or aminosulfonyl;

$R_3$ and $R_4$ are independently H, $C_{1-6}$ alkyl, or together comprise $C_{2-5}$ cycloalkyl, optionally substituted by $C_{1-6}$ alkyl;

X=NR$_5$ or O;

n is 0, 1 or 2; and $R_5$ is hydrogen or alkyl of one to six carbon atoms.

2. A compound as recited in claim 1 wherein X is NH.

3. A compound as recited in claim 2 wherein Z is Z-8.

4. A compound as recited in claim 3 selected from the group consisting of
1'2'-dihydro-N-(8-methyl-8-azabicyclo[3.2.1]octan-3-yl)-2'-oxo-spiro-[cyclopropane-1,3'-(3'H)-indole]-1'-carboxamide, hydrate hydrochloride and 2,3-dihydro-3,3-dimethyl-N-(8-methyl-8-azabicyclo[3.2.1]octan-3-yl)-2-oxo-1H-indole-1-carboxamide, hydrochloride hydrate.

5. A compound as recited in claim 2 wherein Z is Z-6.

6. A compound as recited in claim 5 wherein the compound is selected from the group consisting of:
syn-N-(1-azatricyclo[3.3.1.1$^{3,7}$]decan-4-yl)-2'-oxo-spiro]cyclopropane-1,3'-[3'H]indole]-1'(2'H)-carboxamide, monohydrochloride; and
anti-N-(1-azatricyclo[3.3.1.1$^{3,7}$]decan-4-yl)-2'-oxo-spiro[cyclopropane-1,3'-[3'H]indole]-1'(2'H)-carboxamide, monohydrochloride.

7. A compound as recited in claim 2 wherein Z is Z-9.

8. A compound as recited in claim 7 which is
N-(1-azabicyclo[2.2.2]octan-4-ylmethyl)-2'-oxo-spiro[cyclopropane-1,3'-[3'H]indole]-1'(2'H)-carboxamide, monohydrochloride.

9. A compound as recited in claim 2 wherein Z is Z-11.

10. A compound as recited in claim 9 selected from the group consisting of:
2'-oxo-N-[2-(hexahydro-1H-pyrrolizin-7a(5H)-yl)ethyl]spiro[cyclopropane-1,3'-[3'H]indole]-1'(2'H)-carboxamide, monohydrochloride; and
2'-oxo-N-[(hexahydro-1H-pyrrolizin-7a(5H)-yl)-methyl]spiro[cyclopropane-1,3'-[3'H]indole]-1'(2'H)-carboxamide, monohydrochloride.

11. A compound as recited in claim 2 wherein Z is Z-10.

12. A compound as recited in claim 11 which is exo-2,3-dihydro-3,3-dimethyl-N-[(hexahydro-1H-pyrrolizin-1S-yl)methyl]-2-oxo-1H-indole-1carboxamide, hydrate hydrochloride.

13. A compound as recited in claim 2 wherein Z is Z-1.

14. A compound as recited in claim 13 which is 2,3-dihydro-3,3-dimethyl-N-(hexahydro-1H-2,5-methanocyclopenta[c]pyrrol- 4R-yl)-2-oxo-1H-indole-1-carboxamide, hydrate hydrochloride.

15. A pharmaceutical composition comprising a therapeutically effective amount of a compound of the formula:

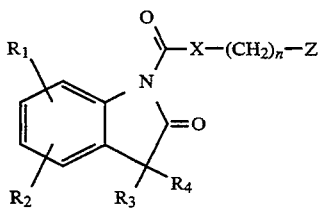

or a pharmaceutically acceptable salt thereof wherein Z is selected from the group consisting of

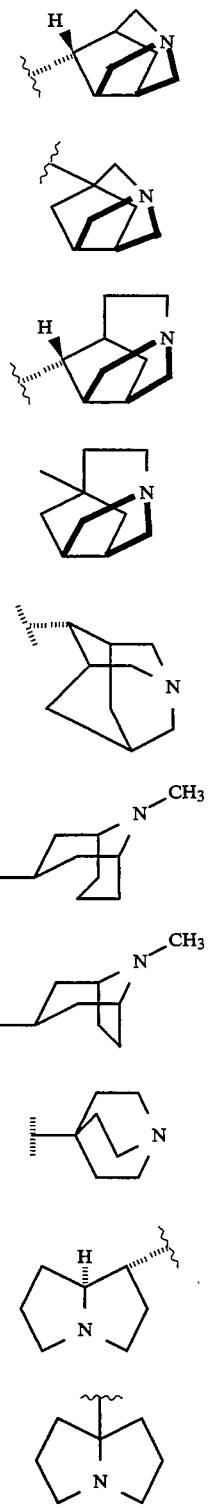

Z-1

Z-2

Z-3

Z-4

Z-6

Z-7

Z-8

Z-9

Z-10

Z-11

$R_1$ and $R_2$ are independently H, halogen, alkyl, aralkyl, amino, alkoxy, alkylthio, acylamino, hydroxy, nitro, aminocarbonyl, or aminosulfonyl;

$R_3$ and $R_4$ are independently H, $C_{1-6}$ alkyl, or together comprise $C_{2-5}$ cycloalkyl, optionally substituted by $C_{1-6}$ alkyl;

X is $NR_5$ or O;

n is 0, 1 or 2;

$R_5$ is hydrogen or alkyl of one to six carbon atoms; and a pharmaceutically acceptable carrier.

16. A pharmaceutical composition as recited in claim 5 wherein the compound is selected from the group consisting of:

endo-2,3-dihydro-3,3-dimethyl-N-(8-methyl-8-azabicyclo[3.2.1]octan-3-yl)-2-oxo-1H-indole-1-carboxamide, hydrochloride hydrate;

endo-1',2'-dihydro-N-(8-methyl-8-azabicyclo[3.2.1]octan-3-yl)-2'-oxo-spiro[cyclopropane-1,3'-(3'H)-indole]-1'-carboxamide, hydrate hydrochloride;

anti-N-(1-azatricyclo[3.3.1.1$^{3,7}$]decan-4-yl)-2'-oxo-spiro[cyclopropane-1,3'-[3'H]indole]-1'(2'H)-carboxamide, monohydrochloride;

syn-N-(1-azatricyclo[3.3.1.1$^{3,7}$]decan-4-yl)-2'-oxo-spiro[cyclopropane-1,3'-[3'H]indole-1'(2'H)-carboxamide, monohydrochloride;

N-(1-azabicyclo[2.2.2]octan-4-ylmethyl)-2'-oxo-spiro[cyclopropane-1,3'-[3'H]indole]- 1'(2'H)-carboxamide, monohydrochloride;

2'-oxo-N-[(hexahydro-1H-pyrrolizin-7a(5H)-yl)-methyl]spiro[cyclopropane-1,3'-[3'H]indole]-1'(2'H)-carboxamide, monohydrochloride;

2'-oxo-N-[2-(hexahydro-1H-pyrrolizin-7a(5H)-yl)ethyl]spiro[cyclopropane-1,3'-[3H]indole]-1'(2'H)-carboxamide, monohydrochloride;

exo-2,3-dihydro-3,3-dimethyl-N-[(hexahydro-1H-pyrrolizin-1S-yl)methyl]-2-oxo-1H-indole-1-carboxamide, hydrate hydrochloride; and 2,3-dihydro-3,3-dimethyl-N-(hexahydro-1H-2,5-methanocyclopenta[c]pyrrol-4R-yl)-2-oxo-1H-indole-1-carboxamide, hydrate hydrochloride.

17. A method of treating conditions responsive to 5-HT$_4$ agonists comprising administering to a mammal in need of such treatment a therapeutically effective amount of a compound of the formula:

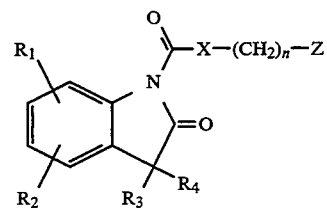

or a pharmaceutically acceptable salt thereof wherein Z is selected from the group consisting of

Z-1

Z-2

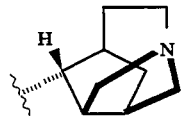

Z-3

-continued

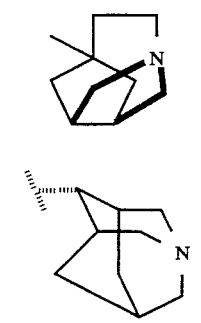

Z-4

Z-6

Z-7

Z-8 and

Z-11

R₁ and R₂ are independently H, halogen, alkyl, aralkyl, amino, alkoxy, alkylthio, acylamino, hydroxy, nitro, aminocarbonyl, or aminosulfonyl;

R₃ and R₄ are independently H, $C_{1-6}$ alkyl, or together comprise $C_{2-5}$ cycloalkyl, optionally substituted by $C_{1-6}$ alkyl;

X=NH; and n is 0, 1 or 2.

18. A method as recited in claim 17 wherein the compound is selected from the group consisting of:
endo-2,3-dihydro-3,3-dimethyl-N-(8-methyl-8-azabicyclo[3.2.1]octan-6S-yl)-2-oxo-1H-indole-1-carboxamide, hydrochloride hydrate;
endo-1',2'-dihydro-N-(8-methyl-8-azabicyclo[3.2.1]octan-3-yl)-2'-oxospiro[cyclopropane-1,3'-(3'H)-indole]-1'-carboxamide, hydrate hydrochloride;
anti-N-(1-azatricyclo[3.3.1.1³,⁷]decan-4-yl)-2'-oxospiro[cyclopropane-1,3'-[3H]indole]-1'(2'H)-carboxamide, monohydrochloride;
endo-N-(1-azatricyclo[3.3.1.1³,⁷]decan-4-yl)-2'-oxospiro[cyclopropane-1,3'-[3H]indole]-1'(2'H)-carboxamide, monohydrochloride;
2'-oxo-N-[2-(tetrahydro-1H-pyrrolizin-7a(5H)-yl)-methyl]spiro[cyclopropane-1,3'-[3H]indole]-1'(2'H)-carboxamide, monohydrochloride;
2'-oxo-N-[2-(tetrahydro-1H-pyrrolizin-7a(5H)-yl)ethyl]spiro[cyclopropane-1,3'-[3H]indole]-1'(2'H)-carboxamide, monohydrochloride;
2,3-dihydro-3,3-dimethyl-N-(hexahydro-1H-2,5-methanocyclopenta[c]pyrrol-4R-yl)-2-oxo-1H-indole-1-carboxamide, hydrate hydrochloride.

19. A method of treating conditions responsive to 5-HT₃ antagonism comprising administering to a mammal in need of such treatment a therapeutically effective amount of a compound of the formula:

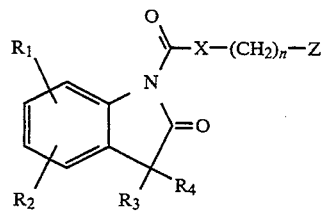

or a pharmaceutically acceptable salt thereof wherein Z is selected from the group consisting of

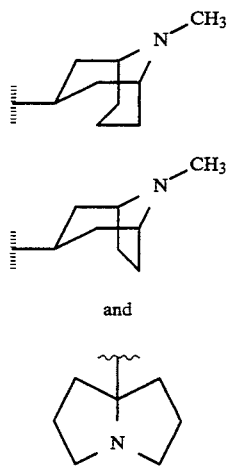

Z-1

Z-2

Z-3

Z-4

Z-6

Z-7

Z-8

Z-9

Z-10

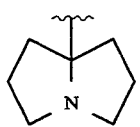

Z-11

R₁ and R₂ are independently H, halogen, alkyl, aralkyl, amino, alkoxy, alkylthio, acylamino, hydroxy, nitro, aminocarbonyl, or aminosulfonyl;

R₃ and R₄ are independently H, $C_{1-6}$ alkyl, or together comprise $C_{2-5}$ cycloalkyl, optionally substituted by $C_{1-6}$ alkyl;

X=NR₅ or O;

n is 0, 1 or 2; and

R₅ is hydrogen or alkyl of one to six carbon atoms.

20. A method as recited in claim 19 wherein the compound is selected from the group consisting of:

endo-2,3-dihydro-3,3-dimethyl-N-(8-methyl-8-azabicyclo[3.2.1]octan-6S-yl)-2-oxo-1H-indole-1-carboxamide, hydrochloride hydrate;

endo-1',2'-dihydro-N-(8-methyl-8-azabicyclo[3.2.1]octan-3-yl)-2'-oxospiro[cyclopropane-1,3'-(3'H)-indole]-1'-carboxamide, hydrate hydrochloride;

anti-N-(1-azatricyclo[3.3.1.1³,⁷]decan-4-yl)-2'-oxospiro[cyclopropane-1,3'-[3H]indole]-1'(2H)-carboxamide, monohydrochloride;

endo-N-(1-azatricyclo[3.3.1.1³,⁷]decan-4-yl)-2'-oxospiro[cyclopropane-1,3'-[3H]indole]-1'(2'H)-carboxamide, monohydrochloride;

N-(1-azabicyclo[2.2.2]octan-4-ylmethyl)-2'-oxospiro[cyclopropane-1,3'-[3H]indole]-1'(2'H)-carboxamide, monohydrochloride;

2'-oxo-N-[(tetrahydro-1H-pyrrolizin-7a(5H)-yl)methyl]spiro[cyclopropane-1,3'-[3H]indole]-1'(2'H)-carboxamide, monohydrochloride;

2'-oxo-N-[2-(tetrahydro-1H-pyrrolizin-7a(5H)-yl)ethyl]spiro[cyclopropane-1,3'-[3H]indole]-1'(2'H)-carboxamide, monohydrochloride;

exo-2,3-dihydro-3,3-dimethyl-N-[(tetrahydro-1H-pyrrolizin-1S-yl)methyl]-2-oxo-1H-indole-1-carboxamide, hydrate hydrochloride; and 2,3-dihydro-3,3-dimethyl-N-(hexahydro-1H-2,5-methanocyclopenta[c]pyrrol-4R-yl)-2-oxo-1H-indole-1-carboxamide, hydrate hydrochloride.

21. A method of treating conditions responsive to 5-HT₄ antagonists or mixed 5-HT₄ agonist/antagonist comprising administering to a mammal in need of such treatment a therapeutically effective amount of a compound of the formula:

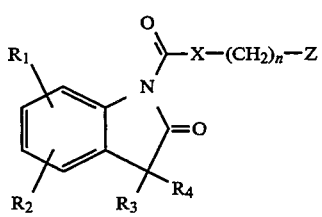

or a pharmaceutically acceptable salt thereof wherein Z is selected from the group consisting of

Z-1

Z-2

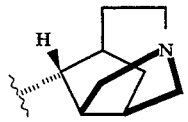

Z-3

Z-4

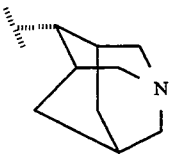

Z-6

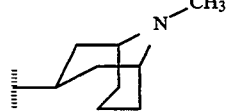

Z-7

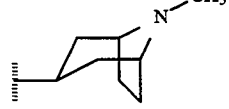

Z-8

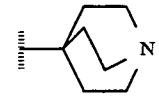

Z-9

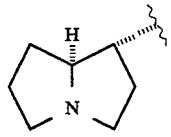

Z-10

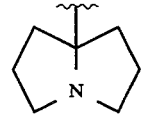

Z-11

R₁ and R₂ are independently H, halogen, alkyl, aralkyl, amino, alkoxy, alkylthio, acylamino, hydroxy, nitro, aminocarbonyl, or aminosulfonyl;

R₃ and R₄ are independently H, $C_{1-56}$ alkyl, or together comprise $C_{1-6}$ cycloalkyl, optionally substituted by $C_{1-6}$ alkyl;

X=NR₅ or O;

n is 0, 1 or 2; and

R₅ is alkyl of one to six carbon atoms.

* * * * *

UNITED STATES PATENT AND TRADEMARK OFFICE
CERTIFICATE OF CORRECTION

PATENT NO.   : 5,399,562
DATED        : March 21, 1995
INVENTOR(S)  : Becker, et al.

It is certified that error appears in the above-indentified patent and that said Letters Patent is hereby corrected as shown below:

Column 3, line 2, reading "5-HT$_3$ agonists" should read -- 5-HT$_4$ agonists --.

Column 3, line 65, the formula reading

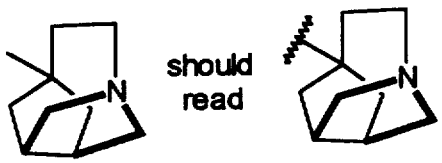

Column 5, line 47, reading "carbooxamide" should read -- carboxamide --.

Column 10, line 2, reading "0 978" should read -- 0.978 --.

Column 10, line 18, reading "to given" should read --to give--.

Column 11, line 41, reading "-2'(1H)" should read ---2'(1'H)--.

Column 12, line 34, reading "indole]-2'" should read -- indol]-2' --.

Column 14, line 5, reading "indole]1'(2'H)carboxamide" should read -- indole]-1'(2'H)-carboxamide --.

Column 14, line 21, reading "indole" should read -- indol --.

UNITED STATES PATENT AND TRADEMARK OFFICE
CERTIFICATE OF CORRECTION

PATENT NO. : 5,399,562
DATED : March 21, 1995
INVENTOR(S) : Becker, et al.

It is certified that error appears in the above-indentified patent and that said Letters Patent is hereby corrected as shown below:

Column 16, line 5, reading "1carboxamide" should read -- 1-carboxamide --.

Column 18, line 64, reading "indole-2-" should read -- indol-2- --.

Column 21, line 22, the formula reading

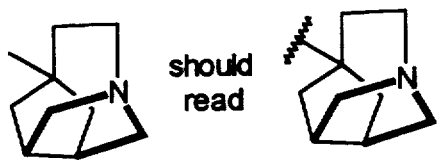

Column 22, line 45, reading "1carboxamide" should read -- 1-carboxamide --.

Column 23, line 20, the formula reading

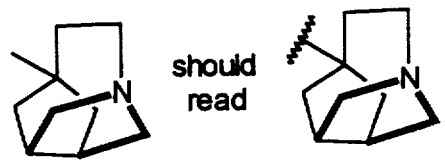

Column 24, line 4, reading "claim" should read -- claim 15 --.

UNITED STATES PATENT AND TRADEMARK OFFICE
CERTIFICATE OF CORRECTION

PATENT NO. : 5,399,562
DATED : March 21, 1995
INVENTOR(S) : Becker, et al.

It is certified that error appears in the above-indentified patent and that said Letters Patent is hereby corrected as shown below:

Column 25, line 4, the formula reading

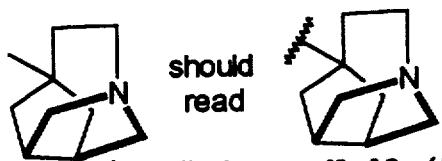

Column 25, line 56, reading "2'-oxo-N-[2-(" should read -- 2'-oxo-N-[( --.

Column 26, line 35, the formula reading

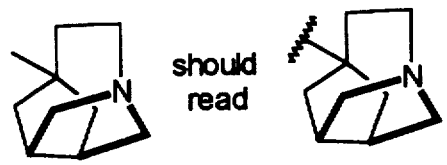

Column 27, line 29, reading "1'(2H)" should read -- 1'(2'H) --.

Column 28, line 20, the formula reading

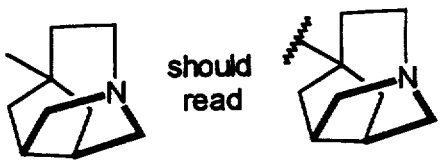

UNITED STATES PATENT AND TRADEMARK OFFICE
CERTIFICATE OF CORRECTION

PATENT NO. : 5,399,562

DATED : March 21, 1995

INVENTOR(S) : Becker, et al.

It is certified that error appears in the above-indentified patent and that said Letters Patent is hereby corrected as shown below:

Column 28, line 62, reading "$C_{1-56}$" should read -- $C_{1-6}$ --.

Column 28, line 63, reading "$C_{1-6}$" should read -- $C_{2-5}$ --.

Signed and Sealed this

Twenty-sixth Day of November 1996

Attest:

BRUCE LEHMAN

Attesting Officer      Commissioner of Patents and Trademarks